United States Patent [19]

Peery et al.

[11] Patent Number: 5,417,976
[45] Date of Patent: * May 23, 1995

[54] DENSITY ELEMENT AND METHOD OF MANUFACTURE THEREOF

[75] Inventors: John R. Peery, Stanford; James B. Eckenhoff, Los Altos, both of Calif.

[73] Assignee: Alza, Palo Alto, Calif.

[*] Notice: The portion of the term of this patent subsequent to Apr. 27, 2010 has been disclaimed.

[21] Appl. No.: 209,024

[22] Filed: Mar. 10, 1994

Related U.S. Application Data

[60] Continuation-in-part of Ser. No. 768,285, Oct. 3, 1991, abandoned, which is a continuation-in-part of Ser. No. 335,028, Apr. 7, 1989, abandoned, which is a division of Ser. No. 591,923, Oct. 2, 1990, abandoned.

[51] Int. Cl.$^6$ ............................................. A23K 1/18
[52] U.S. Cl. ............................... 424/438; 424/473
[58] Field of Search ................................. 424/438, 473

[56] References Cited

U.S. PATENT DOCUMENTS

| | | | |
|---|---|---|---|
| 3,056,724 | 10/1962 | Marston | 424/438 |
| 3,616,758 | 11/1971 | Kamarov | 102/92 |
| 3,844,285 | 10/1974 | Laby | 128/260 |
| 3,948,263 | 4/1976 | Drake Jr. et al. | 128/260 |
| 4,218,255 | 8/1980 | Baipai et al. | 106/45 |
| 4,381,780 | 5/1983 | Holloway | 604/892 |
| 4,449,981 | 5/1984 | Drake et al. | 604/890 |
| 4,505,711 | 3/1985 | Lucas | 604/892 |
| 4,578,263 | 3/1986 | Whitehead | 424/15 |
| 4,595,583 | 6/1986 | Eckenhoff et al. | 424/15 |
| 4,612,186 | 9/1986 | Eckenhoff et al. | 424/15 |
| 4,623,345 | 11/1986 | Laby | 604/892 |
| 4,642,230 | 2/1987 | Whitehead et al. | 424/15 |
| 4,643,893 | 2/1987 | Ascher et al. | 424/16 |
| 4,662,879 | 5/1987 | Drake et al. | 604/892 |
| 4,670,248 | 6/1987 | Schricker | 424/19 |
| 4,671,789 | 6/1987 | Laby | 604/59 |
| 4,675,174 | 6/1987 | Eckenhoff | 424/15 |
| 4,684,524 | 8/1987 | Eckenhoff et al. | 424/469 |
| 4,732,764 | 3/1988 | Hemingway | 424/438 |
| 4,765,837 | 9/1988 | Whitehead | 75/249 |
| 5,206,024 | 4/1993 | Peery | 424/438 |

FOREIGN PATENT DOCUMENTS 59-83703  5/1984  Japan ................. B22F 3/10

OTHER PUBLICATIONS

Sands et al., "Powder Metallurgy Practice and Applications" pp. 8–9, 42–43, 78–107, 124–127, 130–131, 212–213.

*Primary Examiner*—D. Gabrielle Phelan
*Attorney, Agent, or Firm*—Steven F. Stone

[57] ABSTRACT

A density element (12) for use in ruminal delivery devices (10) which is manufactured by partial sintering in such a manner as to fragment upon contact with the many parts in rendering machinery without damage to the blades. The density element (12) has density of at least about 1.5 gm/cm$^3$ and a transverse rupture strength greater than about 3000 psi no greater than about 30,000 psi. The part is sintered under conditions which do not permit full weld bond strength to be obtained and may thereafter be heat treated or impregnated with an inert hydrophobic material to increase corrosion resistance.

14 Claims, 1 Drawing Sheet

DENSITY ELEMENT AND METHOD OF MANUFACTURE THEREOF

CROSS-REFERENCE TO RELATED APPLICATION

This application is a continuation-in-part of U.S. patent application Ser. No. 07/768,285, filed Oct. 3, 1991, now abandoned which was a continuation-in-part of application Ser. No. 07/335,028, filed Apr. 7, 1989, now abandoned, which was a division of U.S. patent application Ser. No. 07/591,923, filed Oct. 2, 1990, now abandoned.

TECHNICAL FIELD

This invention relates to ruminal drug delivery devices and particularly to density elements for such devices and methods for their manufacture.

BACKGROUND OF THE INVENTION

Ruminant animals, including cattle, sheep, giraffe, deer, goats, bison and camels, and more particularly the domesticated species comprise an important group of animals that require periodic administration of medicines, nutrients and other biologically active agents (which are hereinafter referred to in their broadest sense as "drugs") for the treatment and alleviation of various conditions and for better health.

Ruminants have a complex three or four compartment stomach, with the rumen being the largest compartment. The rumen, including the reticulum (hereafter referred to as the "rumen") serves as an important organ for locating dispensing device for delivering medicines and nutrients to such animals over extended periods of time.

There are numerous ruminal delivery devices known in the art which are capable of prolongedly releasing drugs. Typically, these devices are swallowed by the ruminant or otherwise mechanically introduced into the rumen by means of a bolus gun for example, and remain therein for a long period of time without being regurgitated or otherwise eliminated. Typical devices are those disclosed in U.S. Pat. Nos. 4,505,711, 4,578,263, 4,595,553, 4,612,186, 4,623,345, 4,642,230, 4,643,393 and 4,675,179 incorporated herein by reference.

In order to insure: that these devices remain in the rumen for a prolonged period of time a density element is often incorporated into the device. Typically, the density element is manufactured from a material such as iron or steel, iron oxide, magnesium, zinc, cobalt oxide, copper oxide or mixtures thereof, metal shot or parts which may be coated with iron oxide, zinc, magnesium alloy, copper oxide, mixtures of cobalt oxide and iron powder and unsintered, compacted metal powders, and the like. Such density elements typically have sufficient density to bring the overall density of the delivery device to a level greater than the density of ruminal fluid (approximately 1 gm/cm$^3$) and typically to an overall density of at least 2 gm/cm$^3$.

In animals such as cattle raised for slaughter the density element will remain in the carcass after slaughter. The rumen and ruminal contents of animals still containing ruminal delivery devices, including their density elements, are typically processed by rendering plants. Rendering plants comprise a highly automated and continuous operation and though such machinery is typically equipped with magnetic retrieval systems, these systems are not always effective for removing the density elements. As a result, the density elements have caused extensive and costly damage to grinder blades, guillotines, rollers and other equipment.

In addition, it has been found that density elements made from materials such as iron, magnesium or zinc which corrode in water or ruminal fluid and generate gases which interfere with the proper operation of fluid activated delivery devices such as those shown in U.S. Pat. Nos. 4,595,553, 4,612,186 and 4,675,174, for example.

DISCLOSURE OF THE INVENTION

It is an object of this invention to provide structurally coherent density elements for ruminal delivery devices having a density sufficient to maintain the delivery device in the rumen of a living animal and also reproducibly fragment into harmless particles without damage to machinery when the density element contacts the rollers and blades in the cutting and grinding equipment of a rendering plant. As used herein, the term "structurally coherent" refers to density elements which are generally monolithic in nature and are physically broken into smaller particles on contact with rendering blades; as distinguished from density elements formed of individual non-coherent elements, such as metal shot, contained in a rupturable container which are dispersed upon contact with rendering blades.

Another object of this invention is to provide structurally coherent density elements having a transverse rupture strength less than or equal to that of bovine or ovine bone.

A further object of this invention is to provide structurally coherent density elements for use in ruminal delivery devices having a density sufficient to maintain the device in the rumen for a long period of time and a transverse rupture strength less than or equal to bone.

It is another object of this invention to provide fluid actuated ruminal delivery devices having corrosion resistant, structurally coherent density elements possessing a transverse rupture strength less than bovine or ovine bone.

It is another object of this invention to provide structurally coherent density elements having a transverse rupture strength greater than "green" strength and no greater than about 30,000 psi.

It is another object of this invention to provide structurally coherent density elements having a transverse rupture strength in the range of about 6,000 psi–30,000 psi.

It is another object of this invention to provide processes for manufacturing structurally coherent density elements that are resistant to corrosion in water or ruminal fluid.

It is another object of this invention to provide processes for manufacturing structurally coherent density elements for use in ruminal delivery devices that will reproducibly disintegrate into small harmless particles upon contact with blades and rollers used in rendering machinery.

According to this invention a metal powder is compressed and thereafter sintered at a temperature below the standard sintering temperature for the metal at which weld bond strength is achieved (hereinafter, "partially sintered"). The partial sintering may be accomplished in either a reducing, inert or oxidizing atmosphere to produce density elements having various properties as will be explained in detail below. If partially sintered in a reducing or inert atmosphere, the density element may thereafter be heat treated in an oxidizing atmosphere to increase corrosion resistance. The partially sintered parts may also be impregnated with an inert, preferably hydrophobic, material such as silicon oil, mineral oil or wax to further increase corrosion resistance. A non-alloyable filler material may also be mixed with the metal powder prior to compression to reduce the inter-particle bond strength of the partially sintered, structurally coherent density element.

BRIEF DESCRIPTION OF THE DRAWINGS

The drawings, which are not drawn to scale, but rather are set forth to illustrate the various embodiments of the invention and wherein like reference numerals designate like parts, are as follows.

DESCRIPTION OF THE INVENTION INCLUDING BEST MODES

This invention will be described with respect to ruminal delivery devices of the type shown in the Figures, but it is not limited to the specific devices disclosed. The ruminal delivery device designs illustrated herein are merely exemplary of devices known to the art as generally described above and the density elements of this invention can be manufactured in any configuration and be adapted to fit in a ruminal delivery device of any type or configuration.

Figure 1:
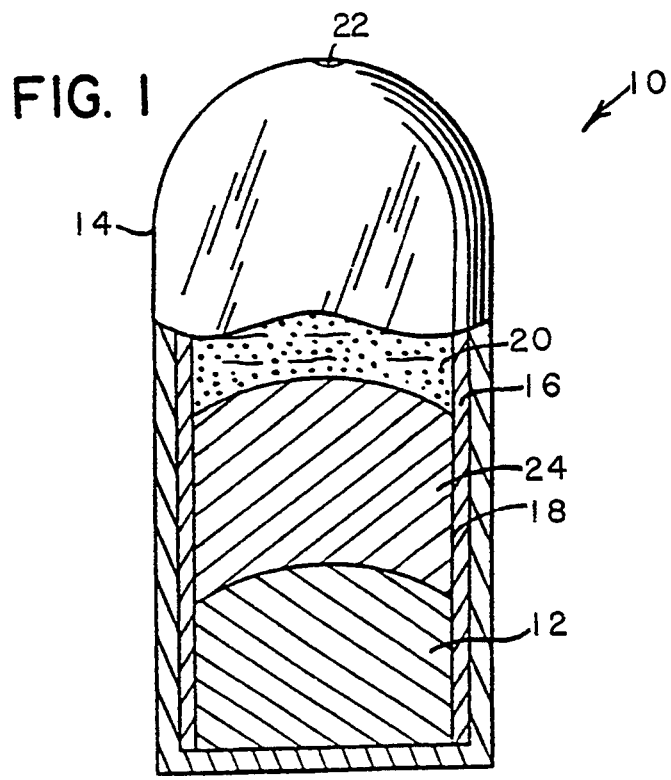
FIG. 1 is a partial cross sectional view of a ruminal delivery device having one embodiment of the structurally coherent density element of this invention.

FIG. 1 shows a fluid activated device 10 of the type described in the patents noted above having a structurally coherent density element 12 at the bottom of the device. The device would also be designed with a wall 14 which surrounds an internal capsule wall 16 and defines an internal lumen 18, which is partially shown in FIG. 1. The agent to be delivered can be dispersed throughout a composition 20, which is delivered through a passageway 22 by pressure exerted upon said composition by a fluid-expandable member 24.

The density element 12 is flat bottomed so as to fit the contour of device 10. However it can have any shape desired and if the ruminal bolus device has a rounded bottom, the density element can likewise be shaped to conform to the curve.

Figure 2:
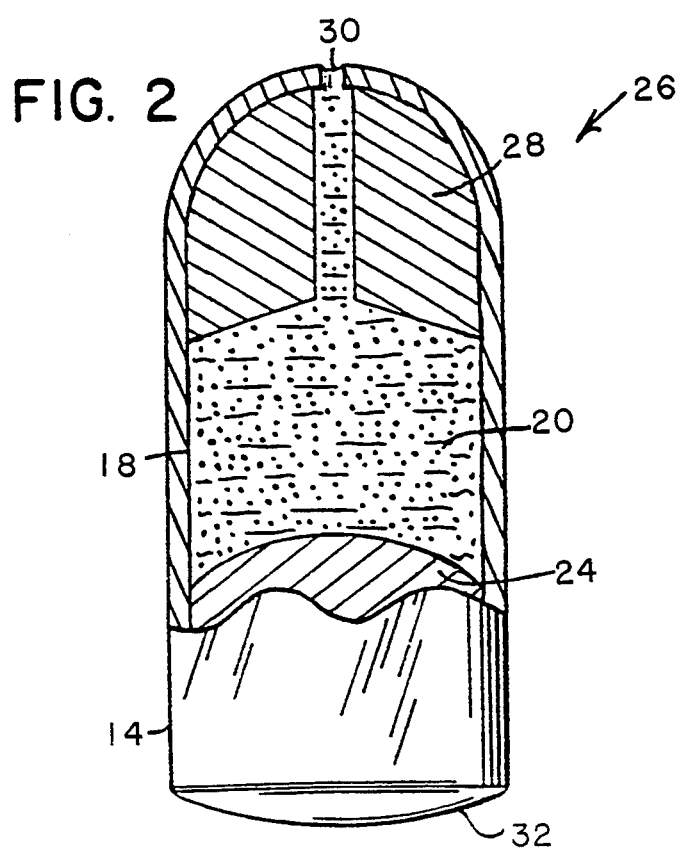
FIG. 2 is a partial cross-sectional view of a ruminal delivery device having another embodiment of the structurally coherent density element of this invention.

This invention also contemplates positioning the density element near the external passageway as is shown in the device 26 of FIG. 2. With the density element 28 so positioned, the passageway 30 extends through the density element 28 to the agent containing composition 20 contained within device 26. For purposes of illustration only, device 26 differs from device 10 by having only a single wall 14 and having a rounded bottom 32.

The structurally coherent density elements of this invention are characterized by having: a) a density sufficient to maintain the delivery device within the rumen of the animal to which it is administered; and b) a transverse rupture strength that will allow the structurally coherent density element to fragment into harmless particles or pieces without damage to rollers, cutting blades or other moving equipment that may contact the density element in the rendering process.

Density elements according to this invention should have a density of at least about 1.5–8 gm/cm$^3$ or higher and preferably the density is within the range of about 2.2 to 7.6 gm/cm$^3$. For ruminal bolus devices which are administered to cattle or sheep, it is preferred to use a density element such that there is a resulting overall density of the delivery device of at least about 3 g/ml.

The structurally coherent density elements of this invention will also have a transverse rupture strength no greater than the maximum strength for which blades in rendering equipment are designed to be capable of rupturing or disintegrating without damage to the equipment. This strength is that of ovine or bovine bone which is approximately 30,000 psi (210 kg/cm$^2$). The structurally coherent density elements of this invention should also have a transverse rupture strength greater than about 3000 psi (210 kg/cm$^2$) which is the maximum strength normally obtained by compaction of the particles in making "green" parts, as discussed below and preferably above about 6000 psi.

Transverse rupture strength of a material is determined by standard ASTM test, ASTM B(378)-7, in which samples of a specified configuration are subjected to a standardized test. Because the density elements of this invention have a different configuration than that utilized in the standard tests, the transverse rupture strength of the elements of this invention may be determined by measuring the transverse rupture strength of standard shaped test samples manufactured under the same conditions as the density elements of this invention.

The transverse rupture strength of parts having non-standard configurations, such as the cylindrical parts of the Figures, may also be determined indirectly from another parameter, radial crush force. In a radial crush test the density element is crushed to yield between two parallel plates and the force at yield measured is measured. Because radial crush force is a geometry dependent property, an initial correlation between radial crush force and transverse rupture strength must be made by tests on samples of the particular geometry having known transverse rupture strengths. Once the correlation is established transverse rupture strength can be determined from radial crush tests of the structurally coherent density elements themselves.

The structurally coherent density element of this invention can be manufactured from any dense, preferably metallic material, which would not react with the ruminal fluid in a manner that would interfere with its functioning as a density element. Iron, because of its density, cost, chemical and biological properties and attraction to magnetic retrieval systems, is preferred according to this invention.

The structurally coherent density elements of this invention are comprised of a partially sintered agglomeration of dense particles, that will reproducibly rupture and disintegrate into component particles, smaller agglomerates or powder upon impact with grinding blades or other energetic components encountered in rendering plants without damaging the equipment.

Sintering is a process of heating small metallic particles to agglomerate them into bulk materials by establishing metallurgical bonds between the particles. The bonds are produced by the formation of a liquid phase between the particles or by solid diffusion between the particles. In typical sintering processes of the prior art, the metallic particles are compressed into the desired configuration to form a compacted, unsintered (hereafter, "green"), relatively fragile part which is thereafter heated for a time and at a temperature sufficient to permit weld bonds to form between the particles. As a result, typical sintering processes produce a metal product which exhibits strength properties approaching those of metals subjected to conventional metallurgical processes which involve melting of the metallic material. The partial sintering process of this invention, however, is conducted under conditions which prevent the formation of full weld bonds and thereby can provide a product having a density similar to that obtained from a typical sintering process but a much lower transverse rupture strength than would be obtained by typical sintering procedures.

The size of the unsintered high density sinterable powder used will affect the density and transverse rupture strength of the finished product and the preferred particle size is 100% < 100 mesh and 85% < 325 mesh. To further reduce the transverse rupture strength of the end product, the sinterable powder can optionally be combined with silica powder or another suitable high density, nonmetallic or non-alloyable metallic filler material that will interfere with the formation of weld bonds between the particles to be sintered. The filler material would have a particle size comparable to that of the sinterable powder and is preferably present in amounts of from 0-50% by volume. A small amount of a lubricant may also be added to the mixture to facilitate uniform compression in the formation of the green part as is known in the sintering art. Suitable lubricants include waxes and oils and may typically be present in amounts of about 0-5% by wt.

The addition of a filler will decrease the transverse rupture strength of the structurally coherent density element and, since typical fillers are less dense than the sinterable material, will also decrease the density. The particle size of the filler material will also have an effect on the strength and density of the finished item and can be varied to obtain the desired combination of density and transverse rupture strength. Generally, larger particle sizes of the material to be sintered and the filler will produce lower density end items and larger filler particles and smaller sinterable particles will produce lower transverse rupture strengths of the finished product.

The sinterable powder/filler particle mixture is compressed into the desired configuration and to approximately the desired density in a suitable die. The compression force should be at least sufficient to provide green strength adequate to permit handling of the part in its green state. Green strength within the range of about 1000-3000 psi and preferably about 1700-1800 psi are suitable. Typically the compression force required to achieve adequate green strength is within the range of about 10-40 tons/in$^2$ and preferably about 30 tons/in$^2$. Green strength is determined by standard ASTM test B(312)-7. Correlations between radial crush force and green strength can also be made in the same manner as described above.

Compression is followed by partial sintering at a temperature below the standard sintering temperature used to achieve weld bond strength for the sinterable material forming the density element. For iron, the preferred partial sintering temperatures according to this invention are in the overall range of about 1100°–1600° F. and preferably at about 1200°–1300° F. for about 1-2 hours. The appropriate temperatures for other materials will also be less than the conventional sintering temperatures for such materials and can be readily determined by workers skilled in the art.

The partial sintering may be performed in either reducing, inert or oxidizing atmospheres which are selected to produce the characteristics desired for the particular density element.

If the partial sintering is performed in a reducing or inert atmosphere the part may thereafter be heat treated in an oxidizing atmosphere. The heat treatment can be performed at temperatures ranging from about 500°–1500° F. to produce an oxidized finish which improves corrosion resistance. The partially sintered part may also be impregnated with an inert, preferably hydrophobic, material such as mineral oil, corn oil, microcrystalline wax or the like to further improve corrosion resistance.

The characteristics obtained from various combinations of partial sintering and heat treatments of iron powder are summarized at Table 1.

TABLE 1

| Partial Sintering Atmosphere @ 1200–1500° F. | Heat Treatment @ 1000–1300° F. in air | Transverse Rupture Strength | Corrosion Resistance | Comments |
|---|---|---|---|---|
| Oxidizing (air) | None | Lowest | Poor | External surface of structure oxidizes closing pore structure. Lubricant vaporizes and emerges under high vapor pressure. Conversely, air does not easily diffuse back in through tight pore structure and interior not oxidized. Lowest inter-particle strength. |
| Inert (Nitrogen) | None | Low | Poor | Lubricant removed. Exterior and interior not oxidized. Low inter-particle bond strength. |
| Inert (Nitrogen) | Yes | Medium Low | Good | Lubricant removed. Exterior and Interior not oxidized. Higher inter-particle bond strength because less oxide present during partial sintering. |
| Reducing (endo gas) | None | Medium | Poor | Lubricant removed. Exterior and interior not oxidized. Higher inter-particle bond strength than in inert gas because of elimination of oxide during partial sintering. |
| Reducing (endo gas) | Yes | Highest | Good | Lubricant removed. interior and exterior oxidized. Highest inter-particle bond strength results from subsequent heat treatment. |

DESCRIPTION OF BEST MODES cl EXAMPLE I

Hollow cylindrical samples configured as shown in FIG. 2, O.D. 0.91, I.D. 0.20 in., length 1.33 in. were formed by compressing 99% wt iron powder (100% < 100 mesh, 85% < 325 mesh) and 1% petroleum based wax lubricant such as Accra Wax in a suitable die at 30 tons/in$^2$ to achieve a green density of 6.83 gm/cm³ and a green strength of 1770 psi. The samples were then partially sintered in an oxidizing atmosphere (air) at 1300°–1500° F. for 1–2 hours. The parts so formed had an oxidized corrosion resistant exterior coating which blocked the pore structure and made subsequent oxidation of the interior impractical. The parts had a crush strength in the range of 1800–2300 pounds which was equivalent, for this configuration, to a transverse rupture strength of about 6,000–7,700 psi. Some of these parts fragmented during normal handling in the subsequent manufacturing process in which delivery devices were fabricated from these elements which indicates that these parts approach the lowest practical strength according to this invention. Structurally coherent density elements manufactured according to this example will fragment without damaging rollers or blades in rendering machinery and are suitable for use in ruminal delivery devices that do not utilize fluid activated dispensing means because measurable hydrogen gas evolution, as a result of corrosion of the unoxidized interior of the density element, will occur when immersed in water or ruminal fluid.

EXAMPLE II

A green density element formed as in Example I was partially sintered in a reducing atmosphere composed of "endo" gas made by cracking natural gas with air over a catalyst at 2050° F. for 30 minutes which was thereafter cooled to approximately 1500° F., forming a mixture of $H_2$, $CO$, $CO_2$ and $N_2$. The parts were partially sintered at about 1400° to 1500° F. for from one to two hours. The wax lubricant was removed during the sintering operation leaving a porous unoxidized structure having a crush strength of approximately 3500 pounds equivalent to a transverse rupture strength of approximately 12,500 psi. Samples so manufactured were subjected to a fragmentation test by impact with a stainless steel tool blade having a 1 millimeter thick edge at a velocity of 2 meters per second. All samples fragmented without damage to the blade which was comparable to blades used in rendering machinery. The samples evolved significant amounts of hydrogen gas upon immersion in a manner similar to the density elements of Example I.

EXAMPLE III

A green density element formed as in Example 1 was partially sintered at about 1300°–1500° F. in nitrogen for one to two hours and thereafter heat treated at 1050°–1350° F. in air. The lubricant was removed during the furnace treatment in nitrogen to produce an open pore structure and both the interior and exterior surfaces of the part were oxidized during the subsequent furnace treatment in air. The part exhibited a crush force of approximately 4000 pounds which is equivalent to approximately 18,500 psi transverse rupture strength. The parts are fragmentable upon impact with blades in rendering machinery and will not evolve measurable quantities of gases that would interfere with the operation of fluid actuated drug delivery devices when immersed either in water or ruminal fluid.

EXAMPLE IV

Green density elements formed as in Example 1 were partially sintered at 1300°–1500° F. for 1 to 2 hours in "endo" gas and thereafter blackened at about 1000°–1300° F. in forced flowing air. The parts possessed a crush force of approximately 6,000 pounds corresponding to a transverse rupture strength of about 20,000 psi. The lubricant was removed during the partial sintering operation and both the interior and exterior of the part were oxidized. Oxide originally present in the green part was removed during the sintering operation resulting in a slightly stronger sintered product than obtained according to Example III. The parts are fragmentable upon contact with the rollers and blades in rendering machinery and were oxidized both interior and exterior. When used as the density element in fluid actuated delivery devices they will not evolve measurable quantity of gasses that would interfere with the operation of the device when exposed to either water or a ruminal fluid.

EXAMPLE V

In an effort to improve the corrosion resistance of density elements formed according to examples I and II, the porous elements were impregnated with a hydrocarbon wax (Multi-wax 180-M) at ambient pressures, positive pressures of 30 psi and in vacuum/pressure at 30 cm Hg/80 psig according to the following procedures:

A. Ambient pressure impregnation
1. Heat density elements and wax separately in a forced air oven to 120° C.
2. Combine wax and density elements for 1 hour.
3. Remove density elements from the 120° C. and immediately direct stream of air, water or steam at the tops of the density elements to blow away the wax hanging up at the tops of the elements.
4. Allow the density elements to cool to room temperature and place (standing upright) on four thicknesses of paper toweling.
5. Place density elements on paper toweling in 120° C. for 30 minutes.
6. Remove density elements while still on the paper toweling and allow to cool. The excess wax aggregate at the bottom of the density element skirt will have been absorbed into the paper toweling.

B. Pressure Impregnation
1. Heat wax in pressure vessel to 120° C.
2. Heat density elements separately at 120° C.
3. Immerse heated density element upright in wax and seal pressure vessel. Bring vessel pressure up to 30 psi with nitrogen.
4. Place vessel in oven at 120° C. for 4 hours.
5. Remove vessel from oven and release pressure slowly.
6. Remove density elements from vessel and blow off excess top surface wax with air, water or steam.
7. Allow to cool at room temperature.
8. Place on paper toweling and put into 120° C. for 30 minutes. Cool density elements to room temperature.

C. Vacuum Impregnation
1. Heat wax in stainless steel beaker to 120° C.
2. Heat density elements at 120° C.
3. Immerse density elements upright in wax and immediately transfer to 120° C. vacuum oven holding at 30 centimeters of mercury for 4 hours.
4. Relieve vacuum.
5. Blow off excess top surface wax with air, water or steam.
6. Allow to cool to room temperature.
7. Place on paper toweling and put into 120° C. oven for 30 minutes.

8. Cool elements to room temperature.

D. Vacuum—Pressure Impregnation

1. Heat wax in a stainless steel vacuum/pressure rated, jacketed tank to 120° C., leaving sufficient head space in tank to accommodate density elements in a wire mesh basket to be later lowered into the molten wax.
2. Place density elements into basket suspended from tank lid by operable lift/lower mechanism (typically hydraulic or air cylinder or screw) sealed against pressure vacuum. Attach lid—basket—densifiers assembly to the top of the tank, thus closing the tank with densifiers inside.
3. Produce 30 cm Hg vacuum within tank and hold while densifiers reach 120° C.
4. Activate lift lower mechanism to immerse hot (120° C.) density elements into molten (120° C.) wax.
5. Reduce vacuum and raise pressure to 80 psi.
6. Hold for 4 hours or longer
7. Reduce pressure to ambient while keeping tank closed.
8. Activate lift/lower mechanism to raise baskets out of molten wax and hold them in the head space above tank to drain excess wax at 120° C.
9. Transfer baskets to another container for exposure to air, steam, or hot water to remove remaining excess wax.
10. Allow the densifiers to cool.

In all cases, the density elements produced according to Example II absorbed wax significantly faster than those produced by Example I. Pressure impregnation either alone or with vacuum was far superior in increasing the amount of wax absorbed than either the ambient or vacuum only impregnation techniques. The pressure impregnated samples manufactured according to Example II exhibited greater corrosion resistance than the unimpregnated samples.

Certain of the techniques employed in process D would be applicable to the commercial manufacture of impregnated density elements according to processes A–C. Placing multiple elements in a movable basket within a pressure vessel containing the wax, heating them simultaneously to 120° C. and then lowering the basket into the molten wax for impregnation makes handling of multiple units simpler. After impregnation, raising the elements from the bath and allowing them to drain at 120° C. eliminates the steps of absorbing the excess wax on toweling and disposing thereof.

EXAMPLE VI

The procedures of Example V are applied to density elements produced according to Examples III and IV. The products so obtained will exhibit a combination of strength and corrosion resistance which makes them the preferred embodiments for use in fluid actuated ruminal delivery devices according to this invention.

EXAMPLE VII

The density elements can also be impregnated at ambient temperatures and pressures if a liquid impregnating material is used. Since an ambient temperature and pressure impregnation has obvious processing advantages, the preferred impregnating composition consists of 84.5% by weight corn oil, 10% ethyl alcohol, 5% lecithin and 0.5% butylated hydroxytoluene mixed to homogeneity in a low shear mixer. The preferred density element is a non-blackened element formed from 99% by weight of iron powder, sieve analyses (U.S. Std.) 60-0%, 100-10.3%, 32.5-69.8) pan-19.9% and 1% wax lubricant compressed to 6.7 g/cm$^3$ and partially sintered for about 30 minutes at 1400–1500 degrees F. in an endo gas or nitrogen atmosphere.

The resulting product was 0.91" O.D., 1.654" long with a 0.20" diameter central bore, tapering externally toward the bore at one end and internally toward the bore at the other end. The product had a crush strength of less than 16,000 pounds of force at yield when crushed between flat plates which was equivalent to a tranverse rupture strength less than 30,000 psi. Elements of this size should be impregnated with from 0.2–0.4 g of the impregnating solution.

The density elements were immersed in the impregnating solution at ambient conditions for approximately 2.5 minutes which is adequate to provide impregnation weights in the desired range.

This invention has been described in detail with particular reference to certain preferred embodiments thereof, but it will be understood that variations and modifications can be affected within the spirit and scope of this invention which is limited only by the following claims wherein:

We claim:

1. A structurally coherent density element for use in a ruminal delivery device said element comprising a partially sintered agglomeration of high density particles having:
   a) a density of at least 1.5 gm/cm$^3$ and;
   b) a transverse rupture strength in the range of 6000 psi to 30,000 psi such that said element fragments upon contact with the blades of rendering machinery without damage to the blades.
2. The density element of claim 1 wherein the density of the element is within the range of 2.2–7.6 gm/cm$^3$.
3. The density element of claim 1 wherein said element comprises partially sintered iron.
4. The density element of claim 3 wherein the surfaces of said density element which are exposed to ruminal fluid are oxidized.
5. The density element of claim 1, 2, 3, or 4 impregnated with an inert hydrophobic material.
6. A ruminal drug delivery device having a density greater than 1.0 gm/cm$^3$ comprising, in combination:
   a) a dose of a drug to be delivered to the rumen of a ruminant animal; and
   b) a density element for maintaining said delivery device in the rumen of said animal, said density element comprising a structurally coherent, partially sintered, agglomeration of high density particles having a density of at least 1.5 gm/cm$^2$ and a transverse rupture strength in the range of 6000 psi to 30,000 psi such that said density element fragments upon contact with moving cutting blades without damage to said blades.
7. The delivery device of claim 6 wherein said density element has a density of from about 2.2–7.6 gm/cm$^3$.
8. The delivery device of claim 6 wherein said density element comprises partially sintered iron.
9. The delivery device of claim 7 wherein said density element comprises partially sintered iron.
10. The delivery device of claim 8 wherein the surface of said density element which are exposed to ruminal fluid are oxidized.
11. The delivery device of claim 6, 7, 8, or 10 wherein said density element is impregnated with an inert hydrophobic material.

12. The delivery device of claim 6, 7, 8 or 10 further comprising:
   c) fluid actuated means for driving said dosage of drug from the devices; and
   d) a density element that is resistant to corrosion by ruminal fluid.

13. The delivery device of claim 10 further comprising fluid actuated means for delivering said dosage from the device.

14. The delivery device of claim 11 further comprising fluid actuated means for delivering said dosage from the device.

* * * * *